United States Patent [19]
Hawkins

[11] Patent Number: 5,179,347
[45] Date of Patent: Jan. 12, 1993

[54] ELECTRICAL SENSOR FOR SENSING MOISTURE IN SOILS

[75] Inventor: Alfred J. Hawkins, Riverside, Calif.

[73] Assignee: Irrometer Company, Inc., Riverside, Calif.

[21] Appl. No.: 866,915

[22] Filed: Apr. 10, 1992

[51] Int. Cl.⁵ ............................................. G01R 27/02
[52] U.S. Cl. .................................... 324/696; 324/694; 73/73
[58] Field of Search ............... 324/663, 664, 686, 689, 324/690, 694, 696, 724, 439, 438, 444, 446, 449, 450; 73/73; 137/78.3

[56] References Cited

U.S. PATENT DOCUMENTS

| | | | |
|---|---|---|---|
| 2,941,174 | 6/1960 | Richards | 324/689 X |
| 4,531,087 | 7/1985 | Larson | 324/696 |
| 4,952,868 | 8/1990 | Scherer, III | 324/664 |

Primary Examiner—Jack B. Harvey
Attorney, Agent, or Firm—Donald D. Mon

[57] ABSTRACT

A soil moisture sensor to be implanted in soil. The sensor has a conductive metal housing, perforated to pass moisture to and through a filter liner which lines an internal cavity. A transfer matrix is confined in the liner and is abutted by a buffer tablet of compacted gypsum. An electrode matrix abuts the tablet and bridges a pair of spaced-apart electrodes. Water, or absence of water, in the electrode matrix provides a measure of moisture in the soil as a function of electrical conductivity between the electrodes.

7 Claims, 1 Drawing Sheet

ELECTRICAL SENSOR FOR SENSING MOISTURE IN SOILS

FIELD OF THE INVENTION

This invention relates to sensors for use in the measurement of moisture in soils.

BACKGROUND OF THE INVENTION

The monitoring of moisture in soils by measuring conductivity between two electrodes is well known. An example is found in Larson U.S. Pat. No. 4,531,087 issued Jul. 23, 1985. The Larson device is typical of sensors which have two spaced-apart electrodes packed in a porous medium, protected by a filter medium which excludes particulates but passes moisture. The conductivity of the medium between the electrodes is measured to reflect the level of moisture in the porous medium.

The conductivity (or electrical resistance) of the region occupied by the porous medium is not a strictly linear function of the moisture content in the soil. Still, properly interpreted it can give the agronomist or gardener valuable information regarding the moisture at some depth in the soil, and can give him guidance concerning the need for irrigation or watering. Simplistically stated, when the porous region is completely dry, there will be no, or at the most minimal, conductivity. A very low or no meter reading will result if current flow is measured. If resistance to a given applied voltage is measured, the inverse of this reading will occur. When the sensor is fully wetted, the conductivity will be at a maximum, and there will be a higher meter reading reflecting this fact.

There is a serious problem. A sensor to be economically practical must be able to function in a wide variety of soils and be responsive to a wide variety of waters. No matter how wet the sensor would be with distilled water, for example, there would always be a low or no reading because conductivity of such water is very low.

It is an object of this invention to provide a sensor whose conductivity is less affected by the variations in concentration of the salts dissolved in soil waters before it reaches the sensitive part of the sensor, and which assures that the water will always have at least some conductivity. The sensor's output is therefore more reliably related to the moisture content of the soil than in previously known sensors such as the Larson sensor.

It is tempting to assume that a sensor of this type should have only two readings- one responsive to no moisture, and another responsive to the presence of sufficient moisture to form a circuit between the two electrodes. Fortunately the actual pattern Is somewhat more complicated. While a graph relating conductivity to moisture content is likelier to be steep in any event, it is not an abrupt curve. As the soil moisture decreases, the conductivity will begin to decrease. It is this decrease and the rate of decrease which the agronomist will watch for, because it will alert him to the fact that the soil is drying out as the consequence of suction exerted by the crop. Properly instrumented, this sensor will give the user adequate notice of the change of moisture content and thus of the demands of the crop. Also, when water is thereafter applied to the soil, a gradual increase in conductivity will signal the rise in the moisture content at the sensor. The rate of change gives information valuable in determining the amount of water to be applied, and at what rate, to satisfy the needs of the crop, as well as to avoid over saturation of the ground with attendant waste of water or excessive loss of water, which could lead to crop damage.

Thus, this sensor is intended as a measurement of the soil moisture at the sensor s level, and of its rate of change.

This invention enables a single sensor to be used for the above purposes in a wide variety of waters, while still providing readings which are consistent with a given meter calibration that can be established at the factory. This is accomplished by providing in the sensor itself a substantial source of electrolyte ions which will assure conductivity whenever moisture is present. It is provided in such a way as to remain effective over a long period of time.

There are other problems solved by this invention. These sensors are placed in soils Which are subjected to occasional variable physical loads, and to stray electrical currents. One can damage or destroy a sensor, and the other can cause faulty or stray readings. This invention provides a strong conductive metal case which resists the physical loads, and which provides a shield that excludes many atray currents. As a consequence, this invention provides a remarkably improved and long-lived sensor to detect soil moisture, and to detect the change and rate of change in moisture content at critical times.

It is another object of this invention to provide a sensor structure which includes only a minimum number of parts, and which can be manufactured to a high degree of consistency from one sensor to another.

BRIEF DESCRIPTION OF THE INVENTION

A sensor according to this invention includes an electrically conductive metal external housing. The housing has a wall with perforations through it to admit moisture to an internal cavity. The wall is peripherally continuous except for the perforations. Thus the housing serves to exclude many or even most stray electrical currents which might give faulty or transient readings.

Preferably the wall is made of a steel alloy, with sufficient thickness and inherent strength of material to withstand substantial weight loads. Stainless steel is a good example.

The housing forms a cavity into which the perforations open. The cavity, where the perforations are located, is lined with a filter grade cloth which will pass water, but which will exclude all but very fine particulates. Inside the liner the cavity contains a transfer matrix, conveniently formed of a silica sand.

A tablet of gypsum (calcium sulphate) is placed against the transfer matrix, and is itself overlaid by an electrode matrix which contains two spaced apart conductive electrodes. The electrode matrix is particulate silica through which moisture can pass and provide a conductive bridge between the electrodes. The gypsum tablet assures that there will be sufficient electrolytes in the moisture that bridges the electrodes to enable a signal to result whenever there is moisture present. In addition, the electrolytes from the gypsum reduce the gross variability of conductance between the electrodes from water to water because they are an additive in relatively constant concentration in waters which waters may initially have very different concentrations of electrolytes from one another (sometimes perhaps very little).

According to a preferred but optional feature of this invention, the sensor is structurally assembled with a crimping procedure which provides for consistency of product.

The above and other features of the invention will be fully understood from the following detailed description and the accompanying drawings, in which:

DETAILED DESCRIPTION OF THE INVENTION

Figure 1:
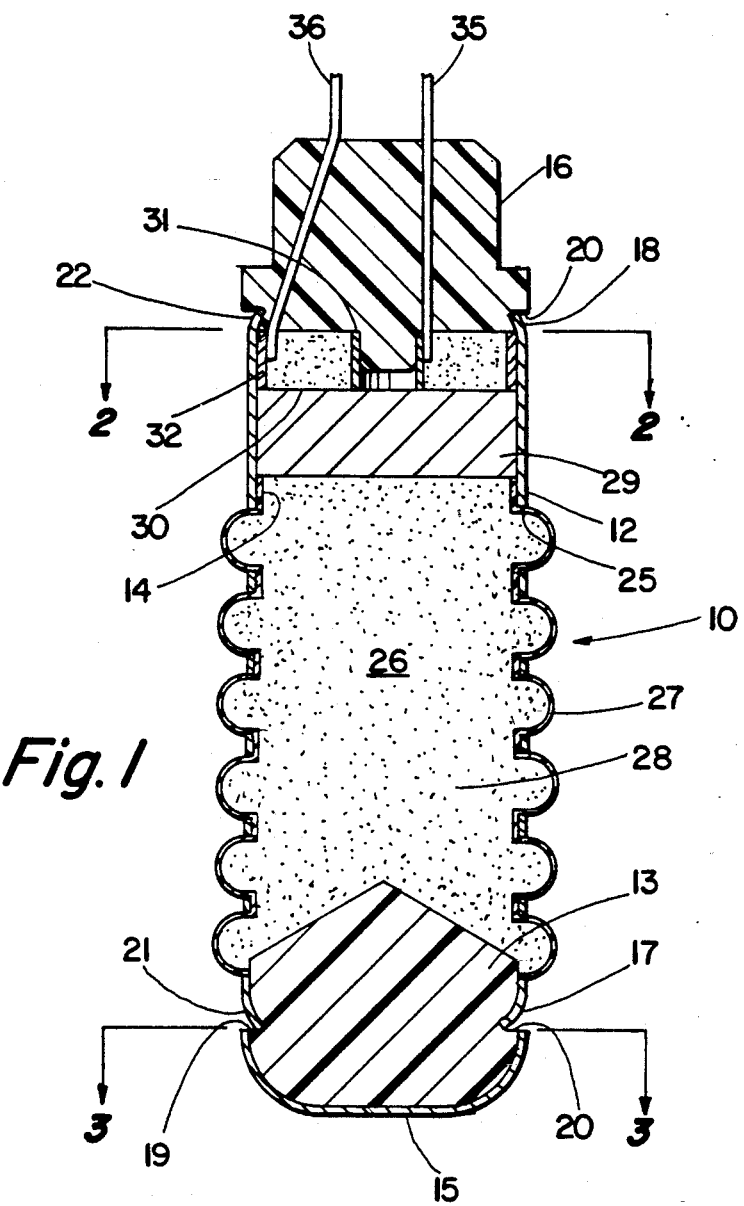
FIG. 1 is an axial cross-section, partially in cutaway cross-section, showing the presently-preferred embodiment of the invention.
Figure 2:
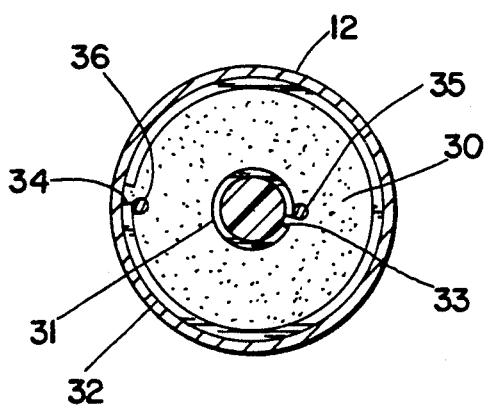
FIG. 2 is a cross-section taken at line 2—2 in FIG. 1.
Figure 3:
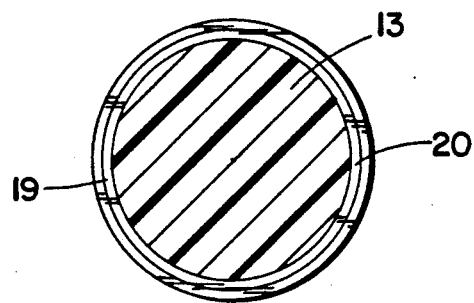
FIG. 3 is a cross-section taken at line 3—3 in FIG. 1.

A sensor 10 according to the invention is shown in FIG. 1. It includes a cylindrical housing 12 with openings 13, 14 at its extremities.

An end cap 15 closes aperture 13. Another end cap 16 closes aperture 14. These caps make a close fit in the openings, and are held in place by crimps 17, 18 on the ends of the housing. The caps have grooves 19, 20 to receive the crimps and are provided with frusto-conical faces 21, 22 against which the crimps can firmly and accurately be pressed. This results in improved consistency in the manufactured product.

The housing is made of conductive metal, such as a nickel-containing stainless steel. It is sufficiently thick, and its material is inherently strong enough, to resist crushing or other distortion, or expulsion of the end caps by physical loads of the type which can be expected in agricultural operations. An example is the passage of a tractor along the surface of ground in which the sensor is buried.

A plurality of perforations 25 is formed through the wall of the housing which give access to an internal cavity 26 inside the wall and between the caps. In a wall about 2½ inches long, and an outer diameter of about ⅞ inches, circular perforations having a diameter of about ⅛ inch give sufficient access for moisture to the cavity, and still the housing will provide an electro-static shield to exclude a substantial portion of the stray currents which tend to flow through the ground in agricultural environments.

A liner 27 constructed of a filter medium lines the inside of the housing wall so as to exclude particulates which would tend to pass through the perforations. A finely woven nylon fabric will serve this purpose and its mesh dimensions can be selected to exclude particulates of any size which would adversely affect the operation of the sensor.

Also, the liner serves to confine a transfer matrix 28 in the cavity. The transfer matrix may conveniently be silica sand, tightly packed in the liner. As shown, this distends the liner into the perforations. This has the additional advantage of assuring a good contact with the soil in which the sensor is buried. Moisture from the soil will pass through the liner and penetrate the transfer matrix.

A buffer tablet 29 bears against the transfer matrix. This buffer tablet is a hard compacted body made of gypsum (calcium sulphate). Gypsum is only slightly soluble in water. Passage of moisture through the tablet will pick up some electrolyte as it passes. This small amount of electrolyte is sufficient to give the water enough conductivity for the sensor assuredly to function whatever the quality of the water. There is only limited flow through the tablet, so the tablet will remain in place and effective for a very long time, even though it can be expected to dissolve away far in the future. An electrode matrix 30 abuts the buffer tablet and receives moisture which has passed through the buffer tablet. It may conveniently be made of silica sand tightly packed in place.

Two electrodes 31, 32 are embedded in the electrode matrix. These are spaced-apart concentric ring-like sections, each with a gap 33, 34. Leads 35, 36 connect to the electrodes. The electrodes will be made of a conductive metal suitably resistant to corrosion. A nickel based stainless steel is useful for this purpose.

Leads pass through cap 16. They are sealed to cap 16 against leakage. They will be connected to any desired instrumentation. For assembly, cap 16 is crimped into place, with the electrodes inside and with the leads passing through cap 16. The electrode matrix material is put in, and is vibrated and compacted to a suitable density. The buffer tablet is next pressed in. The liner will either have already been in place or will now be put in. Then transfer matrix material is put in, vibrated and compacted to a suitable density. This action will cause some distension of the liner into the perforations. Then end cap 13 will be pressed into the respective opening, and this end of the housing will be crimped to hold it. The contacts will be finely packed in the assembled product. Assembly is now complete.

Sensors for the same purpose as this one are known which have gypsum mixed with silica sand in an electrode matrix. While these sensors have functioned under most circumstances, it appears that the use of a gypsum buffer tablet offers more certainty that there will be a suitable electrolyte concentration. This assures that the sensor can function in any kind of water.

There will of course be no conductivity between the electrodes when the electrode matrix is completely dry. This is indicative of dry soil at the sensor's depth. When the electrode matrix is fully wetted, there is maximum conductivity. A meter in a suitable electrical circuit can read out the conductivity (or its inverse, the resistance) between the electrodes, and an indication of moisture content can be obtained.

However, the reading does not abruptly rise or fall with the entry or loss of water in the sensor. Instead the rate of change is generally slow as water enters or leaves the electrode matrix. Loss of water in the sensor (and thus in the electrode matrix) is primarily a consequence of a physical property of soil water known as "matric potential", sometimes referred to as "soil water suction". As wetted soil dries out, principally because the crop is mining water from the soil through its root system, the matric potential increases. This sensor measures the matric potential indirectly- by sensing the conductivity in the electrode matrix (or its inverse, the resistance).

The rate of change of the sensor condition is indicative of the rate at which water enters or leaves the soil. This data is of substantial importance to the agronomist, because he can predict the water needs of the soil, and provide just the correct amount of water at just the correct rate. A reliable sensor, useful with all kinds of water, is obviously of great utility to him, and this invention provides such a sensor.

Further, this sensor is strong enough to resist substantial physical loads. Because the housing us electrically conductive, stray currents in the ground can substantially be excluded from the electrodes. The crimping type assembly assures a tight assembly which does away with assembly bolts and the like, and enables a consistent product to be manufactured.

This invention is not to be limited by the embodiment shown in the drawings and described in the description, which is given by way of example and not of limitation, but only in accordance with the scope of the appended claims.

I claim:

1. A sensor for sensing moisture in soil, comprising:
   a conductive metal housing having a wall which forms an internal cavity, said wall having a plurality of perforations therethrough;
   a porous filter liner lining said wall in said cavity;
   a granular transfer matrix comprising silica sand contained by said liner;
   a buffer tablet of compacted gypsum abutting said transfer matrix;
   an electrode matrix comprising silica sand abutting said buffer tablet;
   a pair of electrodes in contact with said electrode matrix, said electrodes being spaced apart from one another, and bridged by said electrode matrix; and
   a lead extending from each of said electrodes;
   said sensor being closed against entry of moisture except through said perforations, whereby moisture from soil in contact with said liner penetrates said liner and transfer matrix and passes through said tablet, dissolving some electrolyte as it does, and enters said electrode matrix so as to form an electrically conductive path between said electrodes, the conductivity or lack of conductivity of the electrode matrix between the electrodes being indicative of the presence or absence of moisture in the soil contiguous to the sensor.

2. A sensor according to claim 1 in which said transfer matrix is packed in said liner so as to cause the liner to protrude into the perforations, thereby to enable portions of the liner to contact soil in which the sensor is placed.

3. A sensor according to claim 1 in which said electrodes are concentric metal rings, axially aligned with one another.

4. A sensor according to claim 1 in which said housing is tubular, and in which closure means comprising a pair of end caps are sealingly and structurally held to the housing to close said cavity.

5. A sensor according to claim 4 in which said housing is tubular with an opening at each end, in which each end cap has an external peripheral groove, said end caps being inserted in respective end openings, and the ends of said housing being crimped into said grooves to hold the sensor assembled.

6. A sensor according to to claim 5 in which said transfer matrix is packed in said liner so as to cause the liner to protrude into the perforations thereby to provide improved contact with the soil.

7. A sensor according to claim 6 in which said electrodes are concentric rings, axially aligned with one another.

* * * * *